United States Patent [19]

Serri

[11] 4,370,761
[45] Feb. 1, 1983

[54] ARTICULATED PROSTHESIS FOR LOWER LIMB

[76] Inventor: Roberto Serri, Via T. Signorini 21, Scandicci (Firenze), Italy

[21] Appl. No.: 266,167

[22] Filed: May 22, 1981

[30] Foreign Application Priority Data

May 28, 1980 [IT] Italy .............................. 9450 A/80
Feb. 27, 1981 [IT] Italy .............................. 9350 A/81

[51] Int. Cl.³ .............................................. A61F 1/08
[52] U.S. Cl. .............................................................. 3/26
[58] Field of Search .................. 3/2, 22, 23, 25, 29, 3/30, 32, 33, 35, 6

[56] References Cited

U.S. PATENT DOCUMENTS

| | | | |
|---|---|---|---|
| 1,102,774 | 7/1914 | Martinchek | 3/35 |
| 2,208,275 | 7/1940 | McCann | 3/29 |
| 2,644,165 | 7/1953 | Grisoni | 3/6 |

FOREIGN PATENT DOCUMENTS

| | | | |
|---|---|---|---|
| 87730 | 8/1959 | Denmark | 3/25 |
| 925908 | 3/1955 | Fed. Rep. of Germany | 3/23 |
| 1161045 | 8/1958 | France | 3/2 |
| 270822 | 1/1930 | Italy | 3/2 |
| 493891 | 5/1954 | Italy | 3/25 |
| 615595 | 1/1961 | Italy | 3/25 |

*Primary Examiner*—Richard J. Apley
*Assistant Examiner*—David J. Isabella
*Attorney, Agent, or Firm*—McAulay, Fields, Fisher, Goldstein & Nissen

[57] ABSTRACT

A prosthesis includes a knee joint having movable elements geared together and rotatable about axes located rearward of a vertical bearing axis of the prosthesis. A foot member is pivoted about a horizontal ankle joint and is urged by a first spring toward the toe-down position and by a second spring toward the toe-up position. The first spring is stronger than the second spring. A tie rod is connected from the knee joint to the first spring to reduce the force applied by the first spring so that, when the knee joint is bent and the foot is raised from the ground to move the prosthesis forward to a straight-knee position, the toe of the foot is raised to clear the ground. The axis of the knee, being in a position aft of the vertical axis, tends to stably support the leg when it is in its weight-bearing position.

4 Claims, 1 Drawing Figure

ARTICULATED PROSTHESIS FOR LOWER LIMB

BACKGROUND OF THE INVENTION

The invention relates to an articulated prosthesis for a lower limb and more particularly to an articulated prosthesis having knee and ankle joints which act in synchronism.

Lower limb prostheses include a thigh-piece connected for vertical rotation with respect to the lower part of the prosthesis by means of a horizontal pin positioned to intersect the vertical bearing axis of the prosthesis. The lower end of the thigh-piece has a knee with an abutting element for controlling the lower part of the limb to prevent unnatural rotation. Such a structure is relatively unstable in supporting the weight of the user's body due to the fact that the pin of the knee joint intersects the bearing axis of the prosthesis with consequent unforseen and uncontrolled rotation of the joint.

In addition to the above problems, the foot in such prostheses is connected for vertical rotation to the top part of the prosthesis by means of a horizontal pin with an elastic means in the heel acting in opposition to an abutment provided in the forward part of the foot. This abutment prevents the toe of the foot from rotating upward when the foot rests on the ground while bringing the other leg forward.

Since the ankle joint is independent of the knee joint, while the prosthesis is brought forward, the toe of the foot is rotated toward the ground, so that the user must raise himself up on the toe of the other foot in order to clear the downward pointing toe of the prosthesis.

OBJECTS AND SUMMARY OF THE INVENTION

Is is an object of the present invention to provide a prosthesis which overcomes disadvantages of the prior art.

It is a further object of the invention to provide a prosthesis which includes means for straightening the knee during walking to spontaneously advance the leg. The invention, as characterized in the claims, solves the problem of stable equilibrium for the prosthesis when it is supporting the weight of the body and, during walking, gives complete and quiet synchronization of bending the knee, raising of the toe of the foot, and straightening the knee for the spontaneous advance of the leg when the foot is raised off the ground. Finally controlled rotation of the foot planted on the ground supports the weight of the body while bringing the other leg forward.

This result has been attained according to the present invention by using a knee joint with two elements vertically rotatable about two parallel horizontal axes. The axes are set back from the bearing axis of the prosthesis and the two elements interengage along matching toothed sections, rigidly connecting the knee and foot joints by associating the elements for the rigid connection with a first antagonistic spring which compresses during bending of the knee and subsequently expands causing the spontaneous advance of the leg, with a second spring which expands during bending of the knee to raise toe, and with a third spring which compresses during compression of the foot and subsequently expands during bending of the knee.

The advantages obtained by the invention consist essentially in that, in the vertical position, the prosthesis assures maximum stability and safety, correctly raising the toe on bending the knee joint thus clearing the ground with the toe, eliminating resistance to the advance of the leg even on uphill ground and eliminating the necessity for raising up on the toe of the other foot. The spontaneous advance of the leg after the bending of the knee greatly reduces the effort of walking with the entire weight of the body resting on the prosthesis. The foot planted on the ground can rotate at the ankle while bringing the other leg forward and thus permits quiet, flowing and harmonious walking.

BRIEF DESCRIPTION OF THE DRAWING

The invention will now be described in greater detail with the aid of the annexed drawing.

DETAILED DESCRIPTION OF THE PREFERRED EMBODIMENT

Figure 1:
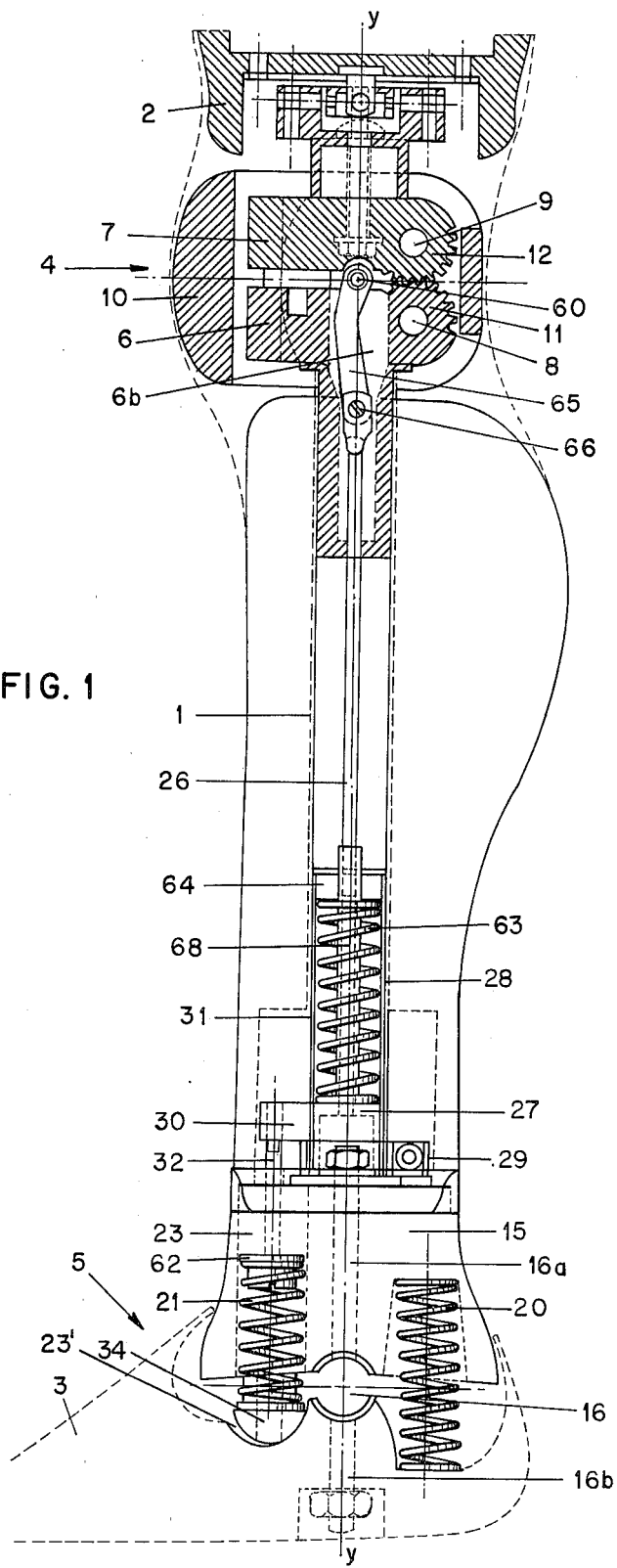
FIG. 1 is a sectional side elevation of the articulated prosthesis according to the present invention.

With reference to the drawing, an articulated prosthesis for lower limb according to the invention includes a tubular post 1, to whose upper and lower ends are connected a knee joint 4 and an ankle joint 5 respectively.

An upper element 2 connects the prosthesis from the thigh to the knee joint 4.

A boot 3 is connected to the ankle joint 5.

Movable elements 6 and 7 provide means for articulation of the knee joint 4. The movable elements 6 and 7 are connected to the post 1 and to the upper element 2 and are rotatable about horizontal and parallel pins 8 and 9. Pins 8 and 9 are supported by a tubular support 10. The pins 8 and 9 are spaced apart and set back from the vertical axis YY of post 1. The ends of the movable elements 6 and 7 around the pins 8 and 9 are cylindrical and have interengaging teeth 11 and 12 on the perimeters thereof so that the elements 6 and 7 cooperate along cylindrical toothed surface portions. The pins 8 and 9 support the weight of the body through tubular support 10.

The ankle joint 5 is formed between the foot 3 and a shin 15. Shin 15 is integral with post 1. A horizontal cylindrical knuckle joint 16 connects shin 15 to foot 3 at an axis intersecting the vertical axis YY of the post 1. First and second threaded stems 16a and 16b, coaxial with the vertical axis YY, are attached to the post 1 and to the foot 3, respectively.

A cranked link rod 65, anchored at the top by a pin 60 to the tubular support 10, passes through the opening 6b beyond the movable element 6 of the knee joint 4 and into the post 1.

A rigid tie rod 26 inside the post 1 is aligned with the link rod 65. The upper end of rigid tie rod 26 is anchored by a pin 66 to the lower end of the link rod 65, and the lower end of the rigid tie rod 26 is anchored by a threaded connection to the top of a pipe 68 coaxial with the post 1.

The top of the pipe 68 passes through an axial hole in a plug 64 fixed atop a sleeve 28. The bottom of the pipe 68 is integral with a piston 27 sliding in the sleeve 28. A lug 30 projects transversely beyond post 1 in a longitudinal opening 31 through post 1 and sleeve 28.

An antagonistic compression coil spring 63 on the pipe 68 is disposed between the plug 64 and piston 27.

A stem 32, parallel to the tie rod 26, is connected at its upper end through a threaded connection to the end of the lug 30. The stem 32 passes vertically through a cylindrical cavity 23 in the shin 15 and is connected at its bottom end to a plate 62 loosely seated inside the cylindrical cavity 23.

A compression coil spring 21 is movably seated in the cavity 23 with its top bearing against the plate 62 and its bottom bearing against a head 34 seated in a hollow 23' of the foot 3.

A compression coil spring 20 inserted between the foot 3 and the shin 15, is set back from the knuckle joint 16 and is weaker than the spring 21.

The operation is as follows.

As the thigh starts forward in the walking direction bringing with it the upper element 2 of the prosthesis, the movable element 6 of the knee joint rotates downward away from the fixed element 7 by rotation of the toothed sector 11 meshed with the toothed sector 12. At the same time the link rod 65 and the tie rod 26 raise the piston 27 with the lug 30, stem 32 and spring 21, thereby compressing the coil spring 63. The thrust exerted by spring 20 raises the toe of the foot 3. As the thigh continues forward and the foot is lifted off the ground, the coil spring 63 expands bringing the post 1 forward to complete closure of the knee joint. When the foot 3 is planted on the ground, the weight of the body rests on the front part of the foot without bending the knee joint due to the offset of pins 8 and 9 from the vertical axis YY. As the leg moves forward bearing the weight of the body, the spring 21 contracts controlling the rotation of the foot 3 and allowing the other leg to be brought forward.

Having described a specific preferred embodiment of the invention with refence to the accompanying drawing, it is to be understood that the invention is not limited to that precise embodiment, and that various changes and modifications may be effected therein by one skilled in the art without departing from the scope or spirit of the invention as defined in the appended claims.

I claim:

1. An articulated prosthesis comprising:
   first means for anchoring said prosthesis to a thigh;
   a knee joint connected to said first means;
   a post connected at its upper end to said knee joint;
   an ankle joint connected to a lower end of said post;
   a foot connected to said ankle joint;
   said post defining a vertical axis;
   said knee joint including first and second vertically aligned horizontal axes, said first and second horizontal axes being disposed rearward of said vertical axis;
   a first movable element in said knee joint affixed to said first means, said first movable element being pivoted on said first horizontal axis and extending forward to intersect said vertical axis;
   a second movable element in said knee joint affixed to said post, said second movable element being pivoted on said second horizontal axis and extending forward to intersect said vertical axis;
   first and second interengaging toothed portions on said first and second movable elements respectively, each toothed portion being concentric with its respective horizontal axis;
   said ankle joint including a third horizontal axis, said vertical axis intersecting said third horizontal axis;
   said foot being rotatable about said third horizontal axis;
   a first vertical spring operative to urge rotation of said foot in a first direction about said third horizontal axis to move a toe of said foot downward;
   a second vertical spring operative to urge rotation of said foot in a second direction about said third horizontal axes to move said toe upward;
   said first vertical spring being stronger than said second vertical spring;
   second means for reducing a force applied by said first vertical spring to a value below a force applied by said second vertical spring when said knee joint is bent whereby said toe of said foot is urged upward to clear the ground when said foot is raised while said prosthesis is moved forward to straighten said knee in preparation for a next step.

2. An articulated prosthesis according to claim 1, wherein said second means includes a tie rod pivoted to said first movable element and passing generally axially through said post, coupling means effective to couple movement of said tie rod to said first vertical spring.

3. An articulated prosthesis according to claim 2, wherein said second movable element includes an opening generally aligned with said vertical axis and said tie rod is pivotally connected to a link rod passing through said opening.

4. An articulated prosthesis according to claim 3, wherein said link rod includes a first pivot at its upper end pivoted to said first movable element and a second pivot at its lower end pivoted to said tie rod.

* * * * *